(12) United States Patent
Chambers

(10) Patent No.: US 10,561,495 B2
(45) Date of Patent: Feb. 18, 2020

(54) SYSTEMS, METHODS AND DEVICES FOR TWO-STEP DELIVERY AND IMPLANTATION OF PROSTHETIC HEART VALVE

(71) Applicant: 4C Medical Technologies, Inc., Maple Grove, MN (US)

(72) Inventor: Jeffrey W. Chambers, Maple Grove, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 67 days.

(21) Appl. No.: 15/876,664

(22) Filed: Jan. 22, 2018

(65) Prior Publication Data

US 2018/0206988 A1 Jul. 26, 2018

Related U.S. Application Data

(60) Provisional application No. 62/449,713, filed on Jan. 24, 2017.

(51) Int. Cl.
*A61F 2/24* (2006.01)
*A61F 2/958* (2013.01)

(52) U.S. Cl.
CPC .......... *A61F 2/2427* (2013.01); *A61F 2/2418* (2013.01); *A61F 2/958* (2013.01); *A61F 2220/0008* (2013.01); *A61F 2250/006* (2013.01)

(58) Field of Classification Search
CPC .... A61F 2/2427; A61F 2/2436; A61F 2/2418; A61F 2/2412; A61F 2002/9528; A61F 2002/9534; A61F 2220/0008; A61F 2220/0025; A61F 2250/006–2250/0063

USPC ...................................... 623/2.11, 2.17–2.19
See application file for complete search history.

(56) References Cited

U.S. PATENT DOCUMENTS

| | | | |
|---|---|---|---|
| 6,425,916 B1 * | 7/2002 | Garrison ............... | A61F 2/2418 623/1.26 |
| 2010/0217382 A1 * | 8/2010 | Chau ...................... | A61F 2/2418 623/1.26 |
| 2011/0112632 A1 | 5/2011 | Chau et al. | |
| 2012/0101571 A1 | 4/2012 | Thambar et al. | |
| 2014/0005778 A1 * | 1/2014 | Buchbinder .......... | A61F 2/2445 623/2.18 |

(Continued)

FOREIGN PATENT DOCUMENTS

| | | |
|---|---|---|
| EP | 2982336 A1 | 2/2016 |
| WO | 2014209232 A1 | 12/2014 |

OTHER PUBLICATIONS

International Search Report and Written Opinion dated Apr. 24, 2018 for PCT Application No. PCT/US18/14774, filed Jan. 23, 2018.

(Continued)

*Primary Examiner* — Paul B Prebilic
(74) *Attorney, Agent, or Firm* — Barnes & Thornburg LLP; Jeffrey R. Stone

(57) ABSTRACT

A two-step delivery method, system and device is disclosed comprising, in various embodiments, a self-expanding frame. A self-expanding frame is delivered and expanded within a heart chamber followed by delivery of a prosthetic valve comprising prosthetic valves thereon into the expanded self-expanding frame, which is in turn connected to a valve connection region defined on and by the delivered and expanded frame.

18 Claims, 1 Drawing Sheet

(56) References Cited

U.S. PATENT DOCUMENTS

| | | | | |
|---|---|---|---|---|
| 2014/0194983 A1* | 7/2014 | Kovalsky | ............ | A61F 2/2418 |
| | | | | 623/2.38 |
| 2014/0277411 A1 | 9/2014 | Bortlein et al. | | |
| 2017/0348098 A1* | 12/2017 | Rowe | ............ | A61B 17/0401 |
| 2018/0200049 A1* | 7/2018 | Chambers | ............ | A61F 2/2439 |

OTHER PUBLICATIONS

International Preliminary Report on Patentability, dated Jul. 30, 2019, for PCT Application No. PCT/US2018/014774.

\* cited by examiner

SYSTEMS, METHODS AND DEVICES FOR TWO-STEP DELIVERY AND IMPLANTATION OF PROSTHETIC HEART VALVE

CROSS-REFERENCE TO RELATED APPLICATIONS

This application claims the benefit of U.S. Provisional Application Ser. No. 62/449,713, filed Jan. 24, 2017 and entitled SYSTEMS, METHODS AND DEVICES FOR ATRIAL ANCHORING FRAME AND CONNECTIVE VALVE SYSTEM AND TWO-STEP IMPLANTATION METHOD.

STATEMENT REGARDING FEDERALLY SPONSORED RESEARCH OR DEVELOPMENT

Not Applicable

INCORPORATION BY REFERENCE

All references, including but not limited to publications, patent applications and patents mentioned in this specification are hereby incorporated by reference to the same extent and with the same effect as if each reference was specifically and individually indicated to be incorporated by reference.

FIELD OF THE INVENTION

The inventions described herein relate to delivery systems, devices and methods for delivering and/or positioning a cardiac valve.

BACKGROUND OF THE INVENTION

The human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of.

Native heart valves may be, or become, dysfunctional for a variety of reasons and/or conditions including but not limited to disease, trauma, congenital malformations, and aging. These types of conditions may cause the valve structure to either fail to properly open (stenotic failure) and/or fail to close properly (regurgitant).

Mitral valve regurgitation is a specific problem resulting from a dysfunctional mitral valve. Mitral regurgitation results from the mitral valve allowing at least some retrograde blood flow back into the left atrium from the right atrium. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and transseptal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

However, known delivery systems, devices and methods still suffer from significant flaws in delivery methodology including, inter alia, positioning and recapture capability and efficiency.

In addition, known "replacement" heart valves are intended for full replacement of the native heart valve. Therefore, these replacement heart valves physically engage the annular throat and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as a supplementary functional valve as well as be fully capable of replacing the native function of a valve that has lost most or all of its functionality. However, the inventive solutions described infra will apply generally to all types and forms of heart valve devices, unless otherwise specified.

Finally, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the annular through) connected from the stent device down through the annular throat, with the sub-annular surface within the left ventricle, the left ventricular chordae tendineae and even into the left ventricle wall surface(s).

Such 2-chamber solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the annulus, annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, the inventive solutions described herein are readily applicable to single or 2-chamber solutions, unless otherwise indicated.

Various embodiments of the several inventions disclosed herein address these, inter alia, issues.

DETAILED DESCRIPTION OF THE INVENTION

Figure 1:
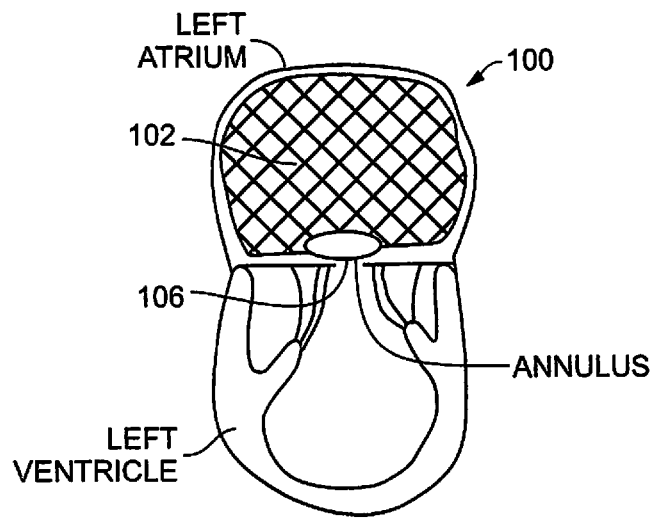
FIG. 1 illustrates a side cutaway view of one embodiment of the present invention.

FIG. 1 illustrates one embodiment of one part of a two-part prosthetic valve device 100 comprising a collapsible left atrial self-expanding frame 102 biased to expand and a collapsible prosthetic mitral valve 104 with prosthetic leaflets attached thereto in a biased expanded configuration that is delivered subsequent to the self-expanding frame 102 with further connection to the self-expanding frame 102 after delivery.

When expanded within the left atrium, at least a portion, e.g., the lower portion of the distal portion of the self-expanding frame 102 anchoring member may be positioned against the upper surface of the annulus within the left atrium as shown. As illustrated, the expanded frame 102 comprises an opening defined by a circumferential (or other shaping) region which is to be used for connecting to the second part of the prosthetic valve, the collapsible and expandable valve. This region is defined as the prosthetic valve, or prosthetic mitral valve, connection region 106, and may comprise a wire or other structure to facilitate connecting with the later-delivered prosthetic valve.

The configuration of FIG. 1, in its various embodiments, thus enables delivery of a frame 102 that may be slightly oversized for the chamber, e.g., left atrium, dimensions through the two-step frame positioning expansion method. Note that the illustrated expanded frame/anchoring member 102 shaping profile assumes roughly the shaping of the atrial chamber itself, with substantial contact on the walls, roof and upper surface of the annulus (super-annular surface) defining at least a portion of the floor of the left atrium and, therefore as described herein the upper annular surface is located within the left atrium. Alternate forms and shapes for the self-expanding prosthetic valve frame, i.e., self-expanding prosthetic mitral valve frame, 102 following expansion may also be used and are within the scope of the present invention so long as the expanded frame serves to anchor the prosthetic valve within the atrial chamber. It is to be understood that the expanded frame 102 may comprise an undeformed shape or profile that differs from the expanded and implanted shape or profile due to anatomical constraints and resistances.

Figure 2:
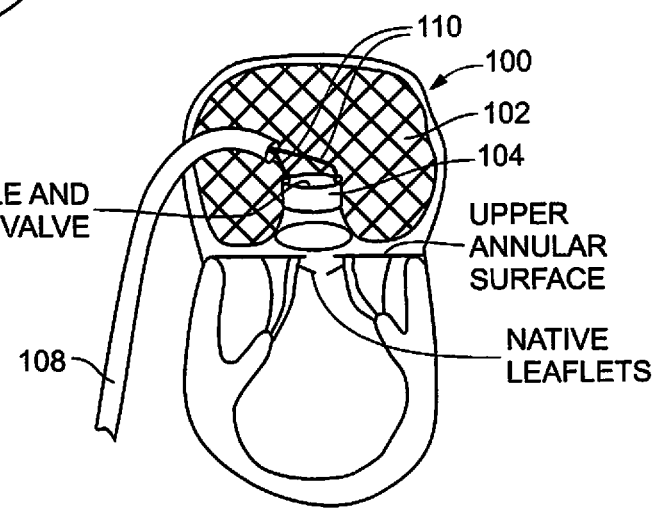
FIG. 2 illustrates a side cutaway view of one embodiment of the present invention.

As shown in FIG. 2, a transseptal catheter delivery technique may be used to deliver the collapsed frame 102 to the atrium, such trans-catheter delivery techniques are well known to the skilled artisan. As the skilled artisan will readily understand, other known types of percutaneous access to the heart chamber, e.g., the left atrium, may be used in combination with the disclosed delivery methods and structures. For example transapical access; transfemoral access, transatrial access, and transseptal access When the collapsed frame 102 is pushed by known techniques beyond the distal opening of the delivery catheter 108, the frame 102 is biased to expand and so expands upon release from the delivery catheter 108. The frame 102 may be delivered so that the valve connection region 106 is positioned to engage the super annular surface and to enable the continuing fluid engagement between the left atrium, annulus and left ventricle when the frame 102 expands.

Turning now to FIG. 2, the self-expanding frame 102 is positioned as expanded and anchored within the atrial chamber, with the mitral valve connection region 102 located generally above the annulus to enable fluid flow therethrough when the prosthetic mitral valve 104, including prosthetic mitral valve leaflets attached thereto, is delivered and connected.

Following positioning expansion and anchoring of the self-expanding prosthetic mitral valve frame 102, the collapsible and expandable prosthetic mitral valve 104 is delivered through the lumen of the catheter which extends through a gap in the catheter framework and into the atrial chamber. Once the prosthetic mitral valve 104 is translated beyond the distal opening of the catheter 108, the valve 104 expands to its biased expanded configuration. As shown, tether wires 110, or other means, may be used to further position the delivered prosthetic mitral valve 104 downward to connect with the prosthetic mitral valve connection region 106 on the frame 102. Such connection may be made with a snap-in place mechanism such as male members on either the valve connection region or the lower surface of the expanded valve 104 that connect with complementary female members on the corresponding part of the prosthetic mitral valve connection region 106. For example, the prosthetic mitral valve connection region 106 may comprise may comprise male members that connect with female members on the lower surface of the delivered prosthetic mitral valve 104. Alternatively, the prosthetic mitral valve connection region 106 may comprise female members that connect with male members on the lower surface of the delivered prosthetic mitral valve 104. This connection embodiment may comprise a locking mechanism once the connection(s) is made.

Alternatively, the two components of the prosthetic valve, i.e., the expanded frame 102 and the delivered valve 104 may be connected by a zip tie like connection wherein the valve 104 may lock into place and further be moved downward into the frame 102 to enable variation of the valve height and/or move it closer to the native mitral valve if desired during the delivery and connecting of the prosthetic mitral valve 104.

Figure 3:
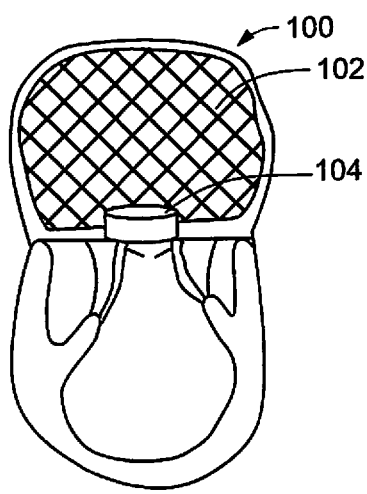
FIG. 3 illustrates a side cutaway view of one embodiment of the present invention.

FIG. 3 illustrates one embodiment of the prosthetic valve device 100 as constructed from the delivered and expanded prosthetic mitral valve frame 102 and connected prosthetic mitral valve 104. A preferred embodiment comprises the prosthetic mitral valve 104 positioned and/or spaced completely above the upper annular surface. Alternatively, the present invention may also comprise the prosthetic mitral valve 102 in a collinear position with the upper annular surface or the prosthetic mitral valve 102 may be positioned below the upper annular surface so that at least a portion of the prosthetic mitral valve 102 is located within the annulus.

As a result, various configurations are possible with the above-described embodiments.

A two-step prosthetic valve device as described above may be provided for replacement and/or supplementation of an existing native heart valve, e.g. the mitral valve or the tricuspid valve. In the embodiment where supplementation is provided, the native valve is allowed to continue functioning with minimal or no engagement or interference by the implanted prosthetic valve device. Further, when the native valve functionality deteriorates sufficiently, the implanted prosthetic valve device may then assume full functionality and completely replace the native valve's functionality. Thus, supplementation, and eventually replacement of native valve functionality is achieved with a single procedure and implant.

Certain embodiments comprise a delivered prosthetic mitral valve device 100 that does not touch, engage and/or interfere with at least one of the left ventricle, tissue within the annulus between the left atrium and left ventricle—also referred to as annular tissue located below the upper annular surface that forms at least part of the floor of the left atrium, and/or the native mitral valve leaflets. These characteristics may be at least partially achieved by locating the expanded prosthetic device 100 on or above the upper annular surface. Further, the prosthetic mitral valve 104 and/or prosthetic mitral valve connection region 106 may be located on, or above, i.e., spaced away from, the native mitral valve.

In other embodiments, the delivered and expanded prosthetic mitral valve device 100, and the prosthetic mitral valve and/or the prosthetic mitral valve connection region 104,106, may be positioned no lower than the upper annular surface. The skilled artisan will recognize that, in some cases, this arrangement may partially engage the native valve leaflets, providing a stop point for the native leaflets as they move upward to coapt, thus establishing a fixed and artificial coaption point for the native leaflets to assist in retaining and maintain the native valve leaflet functionality for as long as possible. Thus, the prosthetic mitral valve connection region, prosthetic valve 104 connected with the prosthetic mitral valve connection region 106 and/or the prosthetic mitral valve leaflets may be located on the upper annular surface.

In other embodiments, a portion of the expanded prosthetic device 100 may extend downward into the annulus and may engage or touch at least one of the left ventricle, the annular tissue below the upper annular surface and/or the native mitral valve leaflets.

Depending on the type of percutaneous access to the heart chamber, e.g., the left atrium, for example transapical access; transfemoral access, transatrial access, and transseptal access, the delivery of the prosthetic heart valve device 100 and its components, may, or may not engage or touch one of the left ventricle, the annular tissue below the upper annular surface and/or the native mitral valve leaflets.

The description of the various inventions, embodiments thereof and applications as set forth herein is illustrative and is not intended to limit the scope of the invention. Features of various embodiments may be combined with other embodiments within the contemplation of these inventions. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the inventions.

What is claimed is:

1. A two-step method of delivering a prosthetic mitral valve device comprising a self-expanding prosthetic mitral valve frame and a prosthetic mitral valve comprising prosthetic mitral valve leaflets to an implantation site within a left atrium of a patient's heart for supplementing and/or replacing the native mitral valve leaflet functionality, comprising:

accessing the left atrium by transseptal access with a delivery catheter having a proximal end, a distal end and a lumen therethrough;

loading the self-expanding prosthetic mitral valve frame in a collapsed configuration into the lumen of the delivery catheter at the proximal end thereof, wherein the collapsed configuration of the prosthetic mitral valve frame comprises:

a prosthetic mitral valve connection region attached thereto, and a section with openings therethrough;

delivering the collapsed self-expanding prosthetic mitral valve frame out of the distal end of the delivery catheter and into the left atrium at a location proximate the implantation site;

allowing the delivered self-expanding prosthetic mitral valve frame to expand within the left atrium at the implantation site, wherein at least a portion of the expanded self-expanding prosthetic mitral valve frame engages at least a portion of the upper annular surface within the left atrium and wherein the prosthetic mitral valve connection region is aligned with the annulus between the left atrium and the left ventricle;

loading the prosthetic mitral valve comprising prosthetic mitral valve leaflets into the lumen of the delivery catheter and delivering the prosthetic mitral valve out of the distal end of the delivery catheter and into the expanded self-expanding prosthetic mitral valve frame;

positioning and connecting the prosthetic mitral valve to the prosthetic mitral valve connection region of the expanded prosthetic mitral valve frame;

ensuring that the left ventricle is not touched at any point by the prosthetic mitral valve device or the delivery catheter; and ensuring that the annular tissue below and downstream of the upper annular surface is not touched at any point by the expanded prosthetic mitral valve frame or the prosthetic mitral valve.

2. The method of claim 1, further comprising providing at least one tether wire attached to the prosthetic mitral valve to assist in the delivery, positioning and connecting of the prosthetic mitral valve to the prosthetic mitral valve connection region, the at least one tether wire operably manipulated by an operator.

3. The method of claim 1, further comprising sizing the self-expanding prosthetic mitral valve frame to achieve a larger width and/or height than the width and/or height of the left atrium when the self-expanding prosthetic mitral valve frame is allowed to achieve an undeformed expansion configuration without resistance.

4. The method of claim 1, wherein the prosthetic mitral valve is collapsible and self-expanding, the method further comprising loading the prosthetic mitral valve in a collapsed configuration into the delivery catheter, wherein the prosthetic mitral valve self-expands when delivered out of the distal end of the delivery catheter and into the expanded self-expanding prosthetic mitral valve frame.

5. The method of claim 1, further comprising increasing or decreasing the spacing of the prosthetic mitral valve leaflets from the native mitral valve leaflets during delivery and connection of the prosthetic mitral valve to the prosthetic mitral valve connection region.

6. The method of claim 1, wherein at least a portion of the delivered prosthetic mitral valve engages at least a portion of the upper annular surface within the left atrium.

7. The method of claim 1, further comprising ensuring that the left ventricle is not touched at any point during the connecting of the prosthetic mitral valve to the prosthetic mitral valve connection region.

8. The method of claim 1, further comprising ensuring that the annular tissue below and downstream of the upper annular surface is not touched at any point by the delivery of the prosthetic mitral valve frame.

9. The method of claim 1, further comprising ensuring that the annular tissue below and downstream of the upper annular surface is not touched at any point by the delivery or connection of the prosthetic mitral valve to the prosthetic mitral valve connection region.

10. The method of claim 1, further comprising ensuring that the native mitral valve leaflets are not touched by the delivery and expansion of the self-expanding prosthetic mitral valve frame.

11. The method of claim 1, further comprising ensuring that the native mitral valve leaflets are not touched by the delivered and expanded prosthetic mitral valve connection region.

12. The method of claim 1, further comprising ensuring that the native mitral valve leaflets are not touched by the delivered and connected prosthetic mitral valve.

13. The method of claim 1, further comprising ensuring that the connected prosthetic mitral valve is located above the upper annular surface of the left atrium.

14. The method of claim 1, wherein the prosthetic mitral valve leaflets are spaced above and away from the native mitral valve leaflets after connecting the prosthetic mitral valve to the prosthetic mitral valve frame.

15. The method of claim 1, further comprising spacing the prosthetic mitral valve connection region of the delivered and expanded prosthetic mitral valve frame above and away from the native mitral valve leaflets.

16. The method of claim 1, further comprising spacing the prosthetic mitral valve connection region of the delivered and expanded prosthetic mitral valve frame above and away from the upper annular surface within the left atrium.

17. The method of claim 1, further comprising locating the prosthetic mitral valve connection region of the delivered and expanded prosthetic mitral valve frame on the upper annular surface within the left atrium.

18. A two-step method of delivering a prosthetic mitral valve device comprising a self-expanding prosthetic mitral valve frame and a prosthetic mitral valve comprising prosthetic mitral valve leaflets to an implantation site within a left atrium of a patient's heart for supplementing and/or replacing the native mitral valve leaflet functionality, comprising:

accessing the left atrium by transseptal access with a delivery catheter having a proximal end, a distal end and a lumen therethrough;

loading the self-expanding prosthetic mitral valve frame in a collapsed configuration into the lumen of the delivery catheter at the proximal end thereof, wherein the collapsed configuration of the prosthetic mitral valve frame comprises:

a prosthetic mitral valve connection region attached thereto, and a section with openings therethrough;

delivering the collapsed self-expanding prosthetic mitral valve frame out of the distal end of the delivery catheter and into the left atrium at a location proximate the implantation site;

allowing the delivered self-expanding prosthetic mitral valve frame to expand within the left atrium at the implantation site, wherein at least a first portion of the expanded self-expanding prosthetic mitral valve frame engages at least a portion of the upper annular surface within the left atrium and at least a second portion of the expanded self-expanding prosthetic mitral valve frame extends into the annulus, and wherein the prosthetic mitral valve connection region is aligned with the annulus between the left atrium and the left ventricle;

loading the prosthetic mitral valve comprising prosthetic mitral valve leaflets into the lumen of the delivery catheter and delivering the prosthetic mitral valve out of the distal end of the delivery catheter and into the expanded self-expanding prosthetic mitral valve frame;

positioning and connecting the prosthetic mitral valve to the prosthetic mitral valve connection region of the expanded prosthetic mitral valve frame; and further comprising:

ensuring that the left ventricle is not touched at any point by the prosthetic mitral valve device; and ensuring that the native mitral valve leaflets are not touched at any point by the expanded prosthetic mitral valve frame or the prosthetic mitral valve.

* * * * *